(12) United States Patent
Edic et al.

(10) Patent No.: US 7,885,372 B2
(45) Date of Patent: Feb. 8, 2011

(54) SYSTEM AND METHOD FOR ENERGY SENSITIVE COMPUTED TOMOGRAPHY

(75) Inventors: Peter Michael Edic, Albany, NY (US); Jonathan David Short, Saratoga Springs, NY (US); John Eric Tkaczyk, Delanson, NY (US); Xiaoye Wu, Rexford, NY (US)

(73) Assignee: Morpho Detection, Inc., Newark, CA (US)

( * ) Notice: Subject to any disclaimer, the term of this patent is extended or adjusted under 35 U.S.C. 154(b) by 11 days.

(21) Appl. No.: 11/952,494

(22) Filed: Dec. 7, 2007

(65) Prior Publication Data
US 2009/0147910 A1 Jun. 11, 2009

(51) Int. Cl.
- A61B 6/03 (2006.01)
- H05G 1/60 (2006.01)
- H05G 1/64 (2006.01)
- G21K 3/00 (2006.01)

(52) U.S. Cl. ............... 378/5; 378/19; 378/98.9; 378/98.11; 378/158

(58) Field of Classification Search ............ 378/19, 378/98.8, 156, 157, 158, 159, 5, 98.9, 98.11; 250/370.09
See application file for complete search history.

(56) References Cited

U.S. PATENT DOCUMENTS

| | | | |
|---|---|---|---|
| 4,686,695 A | | 8/1987 | Macovski |
| 4,893,015 A | * | 1/1990 | Kubierschky et al. ........ 250/369 |
| 5,301,266 A | * | 4/1994 | Kimura ....................... 345/660 |
| 5,303,281 A | * | 4/1994 | Koller et al. ................. 378/134 |
| 5,400,379 A | * | 3/1995 | Pfoh et al. ..................... 378/19 |
| 5,570,403 A | * | 10/1996 | Yamazaki et al. .............. 378/5 |
| 5,841,832 A | * | 11/1998 | Mazess et al. ................. 378/56 |
| 5,841,833 A | * | 11/1998 | Mazess et al. .............. 378/98.9 |
| 6,252,932 B1 | * | 6/2001 | Arakawa ................... 378/98.9 |
| 6,332,015 B1 | * | 12/2001 | Honda ..................... 378/98.11 |
| RE37,536 E | | 2/2002 | Barnes |
| 6,418,193 B1 | * | 7/2002 | Albagli ....................... 378/158 |
| 6,611,578 B2 | * | 8/2003 | Snoeren et al. ............. 378/158 |
| 6,650,730 B2 | * | 11/2003 | Bogatu et al. ............... 378/158 |

(Continued)

FOREIGN PATENT DOCUMENTS

DE 4209376 A1 9/1993

(Continued)

OTHER PUBLICATIONS

PCT International Search Report dated Feb. 12, 2009.

(Continued)

*Primary Examiner*—Allen C. Ho
(74) *Attorney, Agent, or Firm*—Armstrong Teasdale LLP

(57) ABSTRACT

An energy-sensitive computed tomography system is provided. The energy-sensitive computed tomography system includes an X-ray source configured to emit an X-ray beam resulting from electrons impinging upon a target material. The energy-sensitive computed tomography system also includes an object positioned within the X-ray beam. The energy-sensitive computed tomography system further includes a detector configured to receive a transmitted beam of the X-rays through the object. The energy-sensitive computed tomography system also includes a filter having an alternating pattern disposed between the X-ray source and the detector, the filter configured to facilitate measuring projection data that can be used to generate low-energy and high-energy spectral information.

17 Claims, 6 Drawing Sheets

U.S. PATENT DOCUMENTS

| | | | |
|---|---|---|---|
| 6,798,864 B2 * | 9/2004 | Petrick et al. | 378/98.8 |
| 6,901,131 B2 | 5/2005 | Edic et al. | |
| 6,904,118 B2 | 6/2005 | Wu et al. | |
| 7,006,679 B2 * | 2/2006 | Funahashi | 382/132 |
| 7,082,182 B2 | 7/2006 | Zhou et al. | |
| 7,426,260 B2 * | 9/2008 | Cantu et al. | 378/98.8 |
| 7,649,981 B2 * | 1/2010 | Seppi et al. | 378/158 |
| 2002/0191751 A1 | 12/2002 | Bogatu et al. | |
| 2004/0102688 A1 | 5/2004 | Walker et al. | |
| 2005/0012046 A1 * | 1/2005 | Groh et al. | 250/370.09 |
| 2005/0084060 A1 * | 4/2005 | Seppi et al. | 378/5 |
| 2008/0247504 A1 | 10/2008 | Edic et al. | |

FOREIGN PATENT DOCUMENTS

| | | |
|---|---|---|
| EP | 138440 A2 | 1/2004 |
| WO | WO9635372 A2 | 11/1996 |

OTHER PUBLICATIONS

Robert E. Alvarez et al. Energy-selective Reconstructions in X-ray Computerized Tomography; Phys. Med. Biol., 1976, 733-744; vol. 21, No. 5.

US Patent Application entitled Dual-Focus X-Ray Tube for Resolution Enhancement and Energy Sensitive CT, U.S. Appl. No. 11/954,295, filed Dec. 12, 2007.

* cited by examiner

SYSTEM AND METHOD FOR ENERGY SENSITIVE COMPUTED TOMOGRAPHY

BACKGROUND

The invention relates generally to computed tomography systems and methods, and more particularly to computed tomography systems and methods utilizing a filter.

Typically, energy-sensitive computed tomography systems employ one of two techniques: acquiring projection data using dual-energy principles, which modulate the spectrum from the X-ray tube by selecting the operating voltage of the X-ray tube or by spectral filtering techniques, or utilizing detector technology to provide energy-sensitive measurements. In one example of the former technique, data is acquired from an object using two operating voltages of an X-ray source to obtain two sets of measured intensity data using different X-ray spectra, which are representative of the X-ray flux that impinges on a detector element during a given exposure time. In general, at least one data set is then processed to represent line integrals of the linear attenuation coefficients of the object along paths of X-ray radiation from the source to the individual detector elements. The measured data that are processed are typically called projections. By using reconstruction techniques, cross-sectional images of the scanned object are formulated from the projections. Utilizing both sets of projection data acquired with different X-ray spectra, line integrals of the density distribution within the field of view of the imaging system of two chosen basis materials can be generated. By using reconstruction techniques, cross-sectional images of the density distributions for both basis materials can be formulated or the effective atomic number distribution within the field of view of the imaging system computed.

X-ray beam attenuation caused by a given length of a material, such as, but not limited to, bone or soft tissue, may be represented by an attenuation coefficient for that material. The attenuation coefficient models separate physical events that occur when the X-ray beam passes through a given length of the material. A first event, known as Compton scatter, denotes the tendency of an X-ray photon, passing through the length of the material, to be scattered or diverted from an original beam path, with a resultant change in energy. A second event, know as photoelectric absorption, denotes the tendency of an X-ray photon, passing through the length of the material, to be absorbed by the material.

Different materials differ in the scatter and absorption properties, resulting in different attenuation coefficients. In particular, the probability of Compton scattering depends in part on the electron density of the imaged particle and probability of photoelectric absorption depends in part on atomic number of the imaged material, i.e., the greater the atomic number, the greater the likelihood of absorption. Furthermore, both Compton scattering and photoelectric absorption depend in part on the energy of the X-ray beam. As a result, materials can be distinguished from one another based upon relative importance of photoelectric absorption and Compton scattering effects in X-ray attenuation by the material. A density distribution and an effective atomic number distribution may be obtained using the two sets of projection data. However, the technique has limitations due to a slow acquisition mechanism since projection data sets corresponding to two separate energy spectra from the X-ray tube must be measured.

In a latter technique, energy sensitive detectors such as, but not limited to, photon counting detectors and dual-layered detectors are used. However, at high count rates, photon-counting detectors experience charge trapping, which limits the absolute incident flux rate that may be accommodated. Furthermore, the dual-layered detectors are not cost effective since two separate detectors are needed to generate the requisite projection data.

Therefore, it is desirable to employ an energy-sensitive computed tomography system that can address one or more of the aforementioned issues.

BRIEF DESCRIPTION

In accordance with an embodiment of the invention, an energy-sensitive computed tomography system is provided. The energy-sensitive computed tomography system includes an X-ray source configured to emit X-rays resulting from electrons impinging upon a target material. The energy-sensitive computed tomography system also includes an object positioned within the X-ray beam. The energy-sensitive computed tomography system further includes a detector configured to receive a transmitted beam of the X-rays traversing through the object. The energy-sensitive computed tomography system also includes a filter having an alternating pattern of multiple attenuating materials disposed between the X-ray source and the detector, the filter configured to facilitate measuring projection data that can be used to generate both low-energy and high-energy spectral information.

In accordance with another embodiment of the invention, a method of energy-sensitive computed tomography imaging is provided. The method includes disposing an X-ray source to emit an X-ray beam resulting from electrons impinging upon a target material. The method also includes disposing an object positioned within the X-ray beam. The method further includes disposing a detector to receive a transmitted beam of the X-rays traversing through the object. The method also includes disposing a filter comprising an alternating pattern of attenuating materials between the X-ray source and the detector, the filter configured to facilitate measurement of projection data that can be used to generate both low-energy and high-energy spectral information.

These and other advantages and features will be more readily understood from the following detailed description of preferred embodiments of the invention that is provided in connection with the accompanying drawings.

DRAWINGS

DETAILED DESCRIPTION

As discussed in detail below, embodiments of the invention include an energy-sensitive computed tomography system and a method for energy-sensitive computed tomography. The computed tomography system disclosed herein includes an imaging method with a filter that can economically provide desired spectral information of an object.

Figure 1:
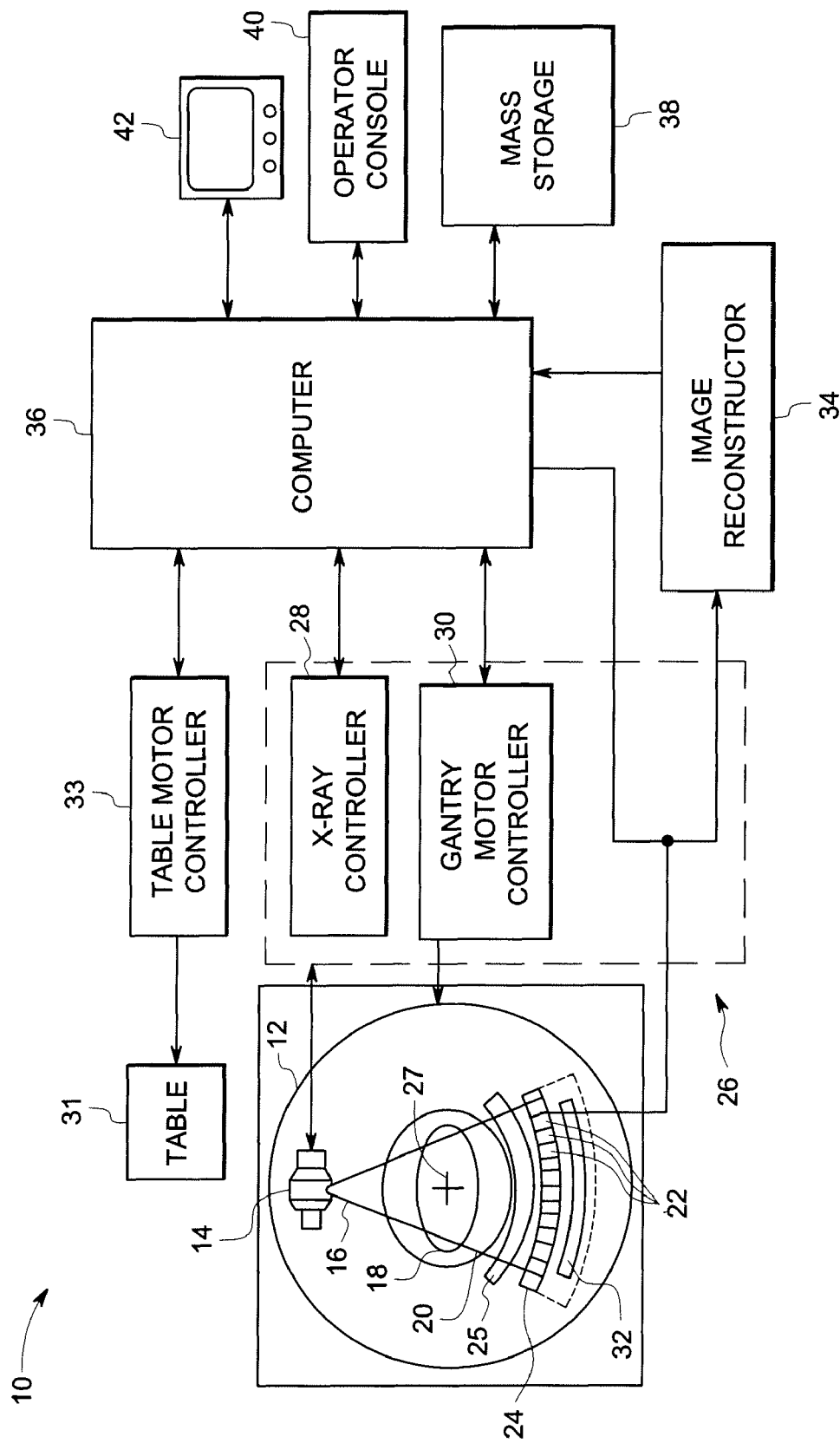
FIG. 1 is a block diagram representation of a computed tomography system including a filter in accordance with an embodiment of the invention.
Figure 2:
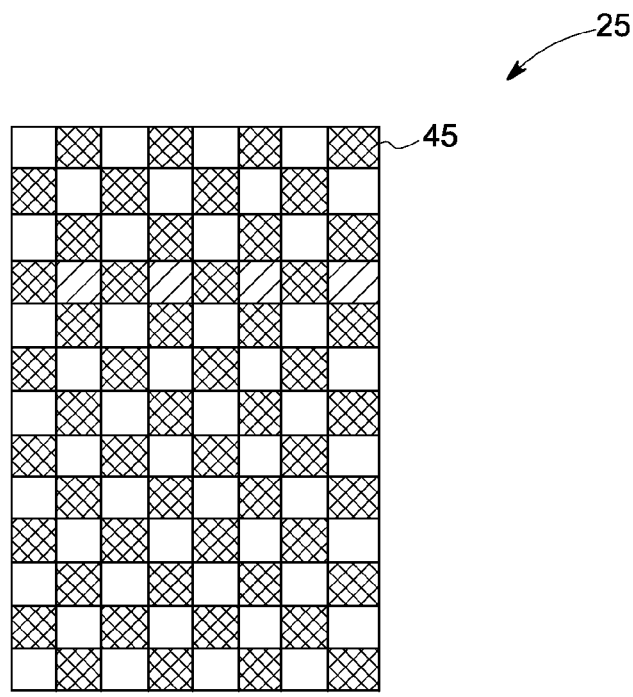
FIG. 2 is a schematic illustration of a filter in the computed tomography system of FIG. 1 having a checkerboard pattern.
Figure 3:
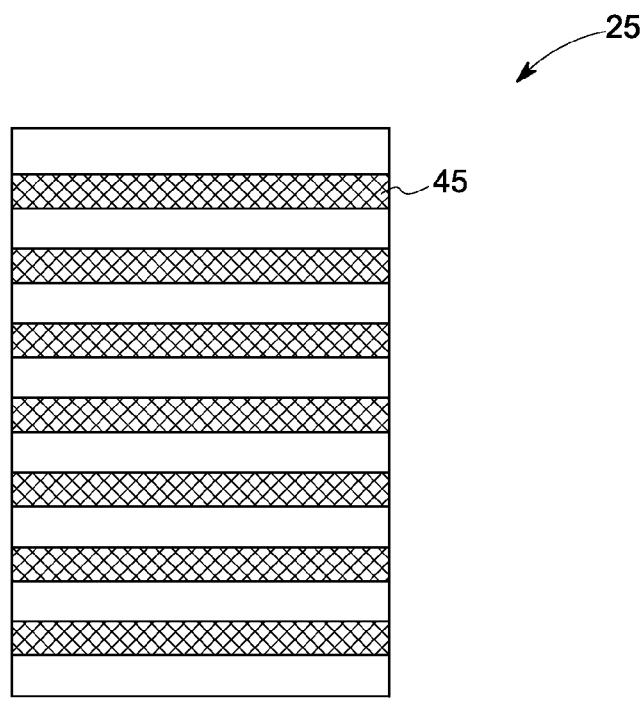
FIG. 3 is a schematic illustration of a filter in the computed tomography system of FIG. 1 having an alternating row pattern.

FIG. 1 is a block diagram representation of a computed tomography system 10. The system 10 includes a gantry 12 having an X-ray source 14 configured to emit an X-ray beam 16 responsive to electrons impinging upon a target material. In an example, the X-ray source 14 is an X-ray tube. In another embodiment, the X-ray source operates at a maximum operating voltage between about 60 to about 200 kV. In yet another embodiment, the maximum operating voltage can be as high as 450 kV. The X-ray beam is incident upon an object 18 resulting in a transmitted X-ray beam 20 through the object 18. Non-limiting examples of the object 18 include a human being, an animal, baggage, and industrial parts. The transmitted X-ray beam 20 through the object 18 is further incident upon a detector 24. The detector 24 includes one or more rows or columns of detector elements 22 that produce electrical signals that represent the intensity of the transmitted beam 20. The electrical signals are acquired and processed to reconstruct an image of the features within the object 18. In a particular embodiment, the detector 24 includes a photon counting detector. In another embodiment, the detector 24 includes a dual-layered detector or energy-integrating detector. A filter 25 having an alternating pattern of multiple attenuation materials such as high-attenuation materials and low-attenuation materials, is disposed between the X-ray source 14 and the detector 24 and outputs a high-energy spectrum in patterned sections containing attenuating material and a total energy spectrum in the patterned regions of little or no attenuation. In the description that follows, the filter comprises alternating sections of attenuating material placed between sections with no attenuating material; however, both sections may comprises attenuating material depending on the desired shaping of the X-ray spectrum. In an example, the high-energy spectrum includes a maximum energy between about 80 to about 200 keV. In an alternative embodiment, the high-energy spectrum includes a maximum energy as high as 450 keV. The filter 25 includes filtering sections arranged alternately such that a high-energy spectrum is outputted when the radiation 20 passes through pixels with the filtering sections, while a total spectrum of the radiation 20 is outputted through pixels without filtering sections.

Rotation of the gantry 12 around a center of rotation 27 and the operation of x-ray source 14 are governed by a control system 26. The control system 26 includes an x-ray controller 28 that provides power and timing signals to the X-ray source 14, a gantry motor controller 30 that controls the rotational speed and position of the gantry 12, and a table motor controller 33 that controls motion of a table 31. An image reconstructor 34 receives sampled and digitized x-ray data from a data acquisition system 32 and performs high-speed reconstruction. The reconstructed image is applied as an input to a computer 36, which stores the image in a mass storage device 38. The image reconstructor 34 may be part of the computed tomography system 10, or may be a remote system.

The computer 36 also receives commands and scanning parameters from an operator via a console 40, which has some form of operator interface, such as a keyboard, mouse, voice activated controller, or any other suitable input apparatus. An associated display 42 allows the operator to observe the reconstructed image and other data from the computer 36. The operator supplied commands and parameters are used by the computer 36 to provide control signals and information to the data acquisition system 32, the X-ray controller 28, the gantry motor controller 30, and table motor controller 33.

Further, the computer 36 records a pair of intensity data measured by alternating detector elements 22 and processed by data acquisition system 32 corresponding to a total energy spectrum and the high-energy spectrum respectively. The computer 36 also interpolates the intensity data of at least one of the high-energy spectrum and the total energy spectrum to obtain interpolated intensity measurements used to generate projection data at a spatial sampling inherent with the original detector configuration. Further, in one embodiment, the computer 36 subtracts the interpolated intensity data of the high-energy spectrum from the total energy spectrum to obtain an intensity data corresponding to a low-energy spectrum. Further, in an alternate embodiment, the computer 36 subtracts the high-energy spectrum from the interpolated total energy spectrum to obtain an intensity data corresponding to a low-energy spectrum. In an exemplary embodiment, the low energy spectrum includes a maximum energy of between about 40 to about 80 keV. Material decomposition and effective atomic number estimation of the object 18 are calculated based upon the projection data generated from measurements from the high-energy spectrum and the low-energy spectrum. Further details of the calculations can be found in co-pending application Ser. No. 11/690245, entitled "System and Method of Density and Effective Atomic Number Imaging", filed on Mar. 23, 2007, and assigned to the same assignee as this application, the entirety of which is incorporated by reference herein. Although discussed with reference to computer 36, the measured projection data can be processed by other computing hardware that is either local to or remote to the imaging system 10.

It should be noted that embodiments of the invention are not limited to any particular computer for performing the processing tasks of the invention. The term "computer," as that term is used herein, is intended to denote any machine capable of performing the calculations, or computations, necessary to perform the tasks of the invention. The term "computer" is intended to denote any machine that is capable of accepting a structured input and of processing the input in accordance with prescribed rules to produce an output. It should also be noted that the phrase "configured to" as used herein means that the computer is equipped with a combination of hardware and software for performing the tasks of the invention, as will be understood by those skilled in the art.

Figure 4:
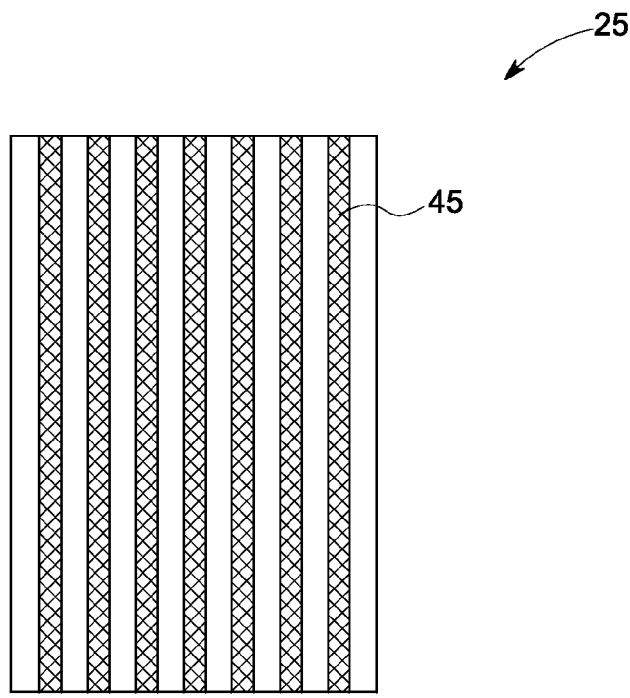
FIG. 4 is a schematic illustration of a filter in the computed tomography system of FIG. 1 having an alternating column pattern.
Figure 5:
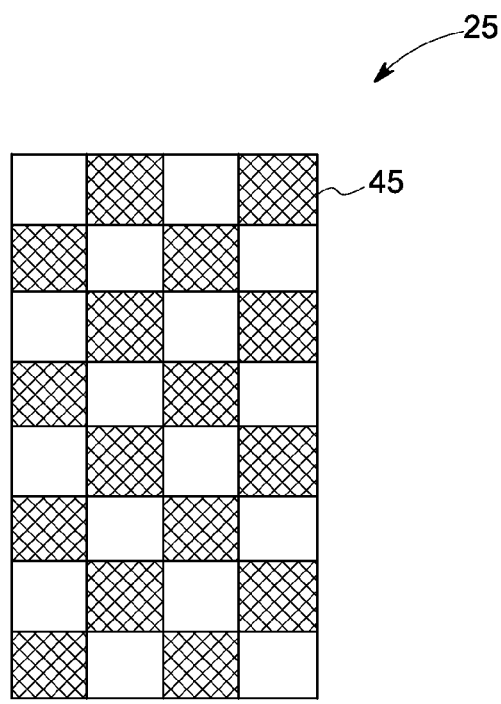
FIG. 5 is a schematic illustration of a filter in the computed tomography system of FIG. 1 having a pack by pack checkerboard pattern.
Figure 6:
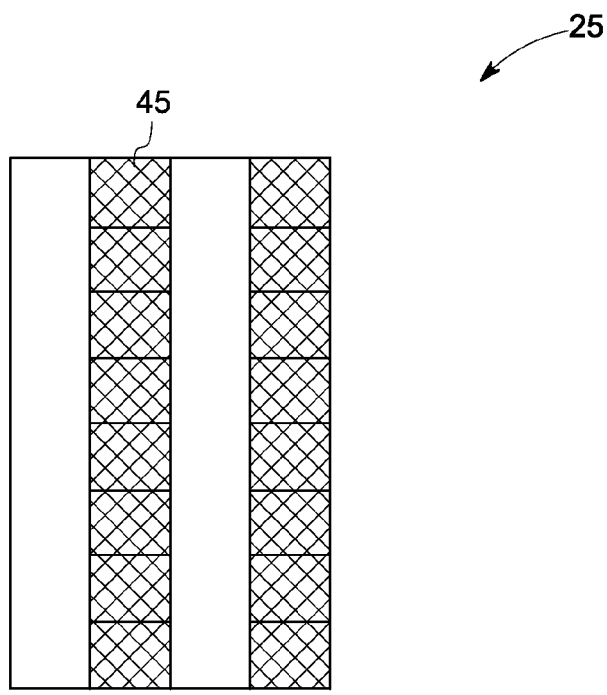
FIG. 6 is a schematic illustration of a filter in the computed tomography system of FIG. 1 having a pack by pack alternating column pattern.
Figure 7:
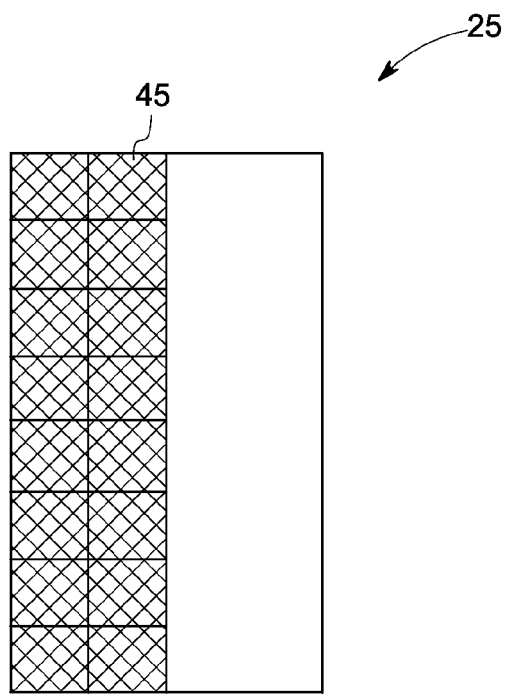
FIG. 7 is a schematic illustration of a filter in the computed tomography system of FIG. 1 having a pattern of alternating sections on the detector.

FIGS. 2-7 are schematic illustrations of the filter 25 having different alternating patterns. The filter 25 includes filtering sections 45 arranged alternately in a checkerboard pattern (FIG. 2) such that intensity data passing through these sections correspond to the high-energy spectrum that is distinct from intensity data corresponding from the total energy spectrum. In an exemplary embodiment, the pattern is chosen to align with boundaries of individual detector elements 22 (FIG. 1). The pattern is also referred to as pixel-to-pixel checkerboard pattern. The filtering sections 45 may be arranged in alternating row patterns (FIG. 3) and alternating column patterns (FIG. 4). In an exemplary embodiment, the pattern is chosen to align with boundaries of individual rows and columns of detector 24, respectively. In another embodiment, the filtering sections 45 are arranged in an alternating pack-by-pack checkerboard pattern (FIG. 5), wherein, in an exemplary embodiment, the patterns align with boundaries of the detector pack. As used herein, the term 'pack' refers to a series of pixels combined into a single package to facilitate the handling and construction of the detector with large area containing many pixels. In yet another embodiment, the filtering sections 45 are arranged pack by pack in alternating columns (FIG. 6) and in alternating sections of the detector 24 (FIG. 7). As mentioned previously, exemplary embodiments using these two configurations maintain alignment between the detector packs and the individual filter elements. Filter materials may be high atomic number sections or layers deposited or applied to the top surface of the detector or to a plastic sheet that is positioned between the X-ray source 14 and the detector 24. The high atomic number layers can be a metal or oxide layer that has high X-ray attenuation for the detector pixels used to measure the high-energy spectral information. In an alternative embodiment, the high atomic number layers may include a K-edge filter leveraging interaction of photons with the K-shell electrons of the material to appropriately shape the spectrum.

Advantageously, embodiments of the invention provide a simultaneous acquisition of high-spectrum data and total-spectrum data. Moreover, the system is cost effective and does not require expensive electronics as compared to alternative techniques. Further, the detector does not limit absolute flux intensity of incident radiation as commonly observed in systems using photon-counting detectors since energy-integrating detector technology can be utilized to measure the high-energy and total-energy signals.

Figure 8:
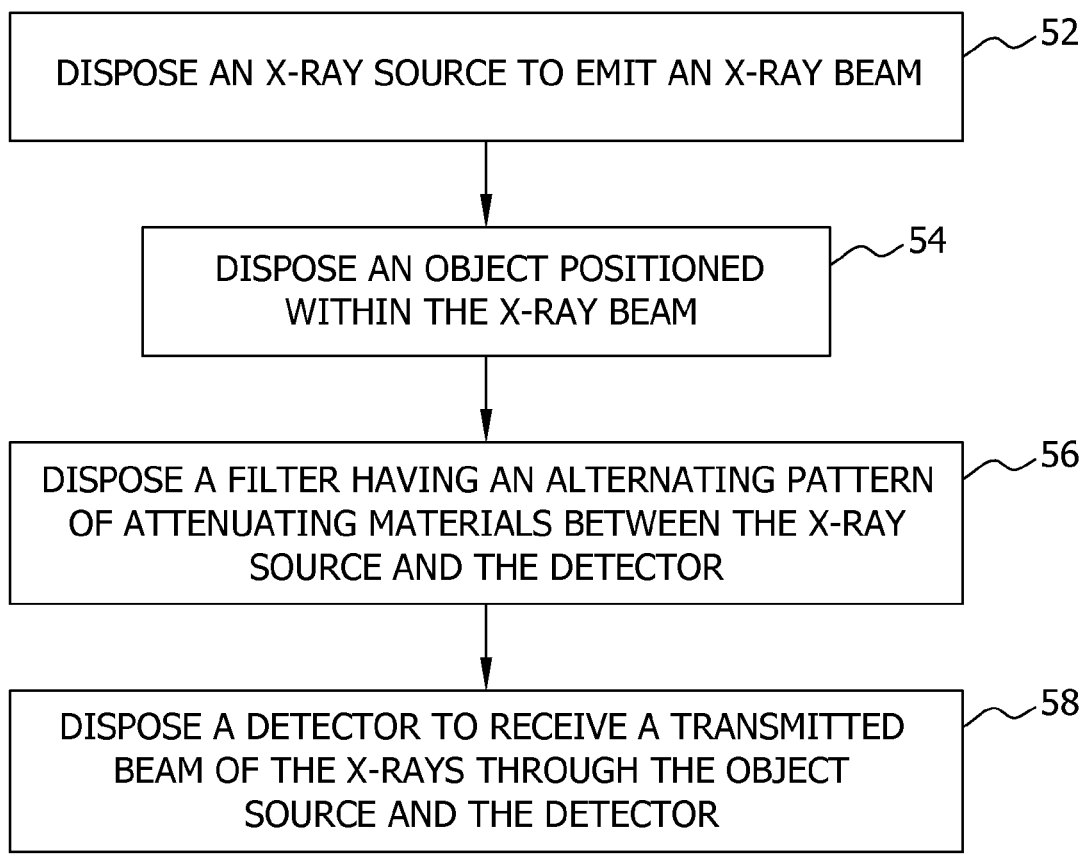
FIG. 8 is a flow chart representing steps in a method for energy-sensitive computed tomography imaging in accordance with an embodiment of the invention.

FIG. 8 is a flow chart representing steps in a method for energy-sensitive computed tomography imaging. The method includes disposing an X-ray source to emit an X-ray beam resulting from electrons impinging upon a target material in step 52. An object is positioned within the X-ray beam in step 54. A filter is also disposed having an alternating pattern of multiple attenuating materials between the X-ray source and the detector to facilitate measurement of projection data that can be used to generate a low-energy and a high-energy spectral information in step 56. In a particular embodiment, the filter is disposed in at least one of a checkerboard pattern, an alternating row pattern, an alternating column pattern, or an alternating pack pattern. Further, a detector is further disposed to receive a transmitted beam of the X-rays through the object in step 58. In a particular embodiment, a photon-counting detector is disposed. In another embodiment, a dual-layered detector is disposed. In yet another embodiment, an energy-integrating detector is disposed. In another embodiment, a computer is coupled to the detector and records intensity data regarding a total-energy spectrum and the high-energy spectrum. The computer also interpolates at least one of the high-energy spectrum and the total-energy spectrum to produce interpolated intensity data, which is used to generate the intensity data corresponding to a low-energy spectrum. The microprocessor further calculates at least one of a material decomposition of the scanned object and an effective atomic number distribution based upon the projection data generated from the high- and low-energy spectral information.

Figure 9:
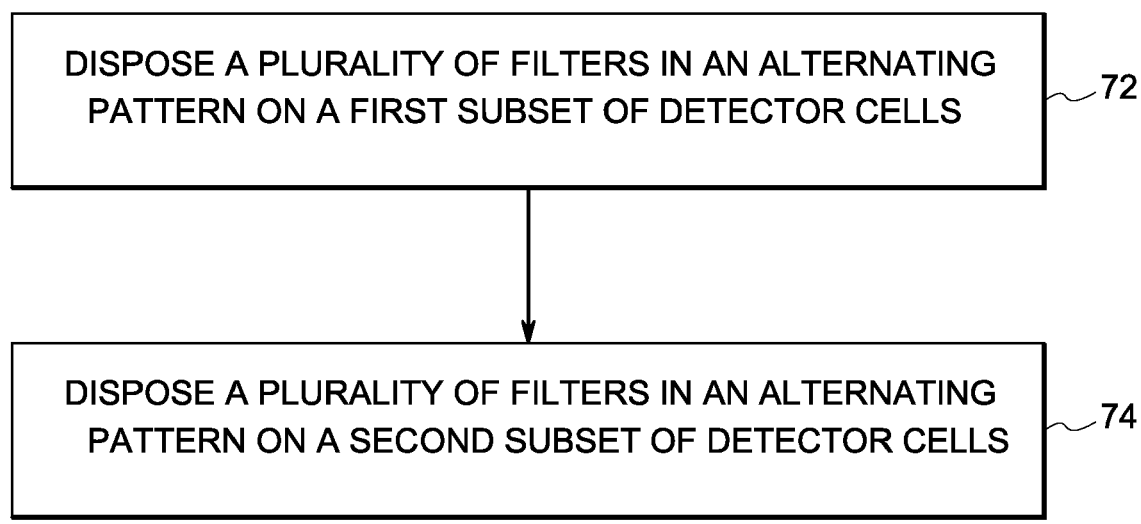
FIG. 9 is a flow chart representing steps in a method for fabricating a detector in a computed tomography imaging system in accordance with an embodiment of the invention.

FIG. 9 is a flow chart representing steps in a method for fabricating a detector in a computed tomography imaging system. The method includes disposing multiple filters in an alternating pattern on a first subset of detector cells in step 72. The filters are configured to generate intensity measurements from a high-energy spectrum of X-ray radiation. The method also includes disposing multiple filters in an alternating pattern on a second subset of detector cells in step 74. Thus, the second subset of detector cells are left exposed to the beam of radiation. In an alternative embodiment, the filters are disposed in alternating rows of the first subset of the detector cells. In another embodiment, the filters are disposed in alternating columns of the first subset of the detector cells. In yet another embodiment, the filters are disposed in a checkerboard pattern of the first subset of the detector cells.

The various embodiments of a system and method for energy-sensitive computed tomography described above thus provide a way to achieve a convenient and efficient imaging means. The technique also reduces false alarm rates significantly in security applications by providing effective atomic number distribution information in addition to standard density image information. Further, the system and technique allow for a cost-effective means of imaging avoiding expensive electronics.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. For example, the use of a photon-counting detector with respect to one embodiment can be adapted for use with a filter having an alternating row pattern described with respect to another. Similarly, the various features described, as well as other known equivalents for each feature, can be mixed and matched by one of ordinary skill in this art to construct additional systems and techniques in accordance with principles of this disclosure.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. An energy-sensitive computed tomography system, comprising:
   a gantry configured to rotate around an object;
   an X-ray source coupled to said gantry and configured to emit an X-ray beam to be incident upon the object;
   a detector coupled to said gantry, said detector comprising a plurality of detector elements configured to receive the X-ray beam transmitted through the object and produce a plurality of signals that represent intensity data of the X-ray beam;
   a filter disposed between said X-ray source and said detector, said filter comprises a first plurality of sections configured to shape a portion of the X-ray beam to be received by a first subset of said plurality of detector elements into a total energy spectrum, and a second plurality of sections configured to shape a portion of the X-ray beam to be received by a second subset of said plurality of detector elements into a high energy spectrum;

a computer coupled to the detector, wherein said computer is configured to:

interpolate intensity data of at least one of the high-energy spectrum and the total-energy spectrum, and determine, from the interpolated intensity data, intensity data corresponding to a low-energy spectrum.

2. The system of claim 1, wherein said filter comprises an alternating pattern of a plurality of attenuating materials.

3. The system of claim 2, wherein the alternating pattern comprises at least one of a checkerboard pattern, an alternating row pattern, an alternating column pattern, and an alternating pack pattern.

4. The system of claim 1, wherein said detector comprises a photon-counting detector.

5. The system of claim 1, wherein said detector comprises an energy-integrating detector.

6. The system of claim 1, wherein the X-ray source is configured to operate at a voltage between 80 kV and 200 kV.

7. A method of energy-sensitive computed tomography imaging, the method comprising:

emitting an X-ray beam from an X-ray source coupled to a gantry configured to rotate around an object;

receiving, via a detector comprising a plurality of detector elements, the X-ray beam transmitted through the object;

provide, via the detector, a plurality of signals that represent intensity data of the X-ray beam;

outputting, via a filter disposed between the X-ray source and the detector, a high-energy spectrum and a total energy spectrum;

interpolating, via a computer, intensity data of at least one of the high-energy spectrum and the total-energy spectrum, and determining, from the interpolated intensity data, intensity data corresponding to a low-energy spectrum.

8. The method of claim 7, wherein the filter comprises at least one of a checkerboard pattern, an alternating row pattern, an alternating column pattern, and an alternating pack pattern of attenuating materials.

9. The method of claim 7, wherein determining, from the interpolated intensity data, intensity data corresponding to a low-energy spectrum comprises subtracting the interpolated intensity data of the high-energy spectrum from the intensity data from the total-energy spectrum or subtracting the interpolated intensity data of the total-energy spectrum from the intensity data from the high-energy spectrum to obtain intensity data corresponding to the low-energy spectrum.

10. The method of claim 9, further comprising calculating at least one of a material decomposition of the object and an effective atomic number distribution within the object based upon intensity data generated from the high-energy spectrum and the low-energy spectrum.

11. The method of claim 7, further comprising operating the X-ray source at a voltage between 80 and 200 kV.

12. The method of claim 7, wherein the detector comprises an energy-integrating detector.

13. The method of claim 7, wherein the detector comprises a photon-counting detector.

14. An energy-sensitive computed tomography system, comprising:

a gantry configured to rotate around an object;

an X-ray source coupled to said gantry and configured to emit an X-ray beam to be incident upon the object;

a detector comprising a plurality of detector elements, said detector configured to receive the X-ray beam transmitted through the object and produce a plurality of signals that represent intensity data of the X-ray beam; and a filter disposed between said X-ray source and said detector, said filter comprising a first plurality of sections configured to shape a portion of the X-ray beam into a first spectrum, and a second plurality of sections configured to shape a portion of the X-ray beam into a second spectrum;

a computer configured to:

receive a plurality of intensity measurements from said plurality of detector elements, wherein said detector facilitates simultaneously measuring an intensity of the X-ray beam transmitted through the object in the first spectrum and an intensity of the X-ray beam transmitted through the object in the second spectrum;

interpolate a set of intensity data of the X-ray beam in the first spectrum and/or the second spectrum; and calculate, from the interpolated set of intensity data and the plurality of intensity measurements, a set of intensity data corresponding to an intensity of the X-ray beam transmitted through the object in a third spectrum.

15. The system of claim 14, wherein said first plurality of sections and said second plurality of sections are disposed in an alternating pattern.

16. The system of claim 15, wherein the alternating pattern comprises at least one of a checkerboard pattern, an alternating row pattern, an alternating column pattern, and an alternating pack pattern.

17. The system of claim 14, wherein the first spectrum is a total-energy spectrum, the second spectrum is a high-energy spectrum, and the third spectrum is a low-energy spectrum.

* * * * *